United States Patent
Watanabe et al.

(10) Patent No.: US 7,718,817 B2
(45) Date of Patent: May 18, 2010

(54) VEGETABLE STEROL ESTER-CONTAINING COMPOSITION AND ADDITIVE THAT INCREASES THE FEELING EFFECTS FROM A HAIR COSMETIC

(75) Inventors: Katsuhiro Watanabe, Tokyo (JP); Toshimitsu Furusawa, Tokyo (JP); Hiroki Kuriyama, Ninomiya-machi (JP); Hiroyuki Suganuma, Odawara (JP)

(73) Assignee: San-Ei Kagaku Co., Ltd., Tokyo (JP)

( * ) Notice: Subject to any disclaimer, the term of this patent is extended or adjusted under 35 U.S.C. 154(b) by 561 days.

(21) Appl. No.: 11/508,350

(22) Filed: Aug. 23, 2006

(65) Prior Publication Data

US 2006/0280764 A1  Dec. 14, 2006

Related U.S. Application Data

(62) Division of application No. 10/858,303, filed on Jun. 1, 2004, now abandoned.

(51) Int. Cl.
*C11B 1/00* (2006.01)
(52) U.S. Cl. .................................... 554/205; 422/800

(58) Field of Classification Search .................. None
See application file for complete search history.

(56) References Cited

U.S. PATENT DOCUMENTS

| | | | | |
|---|---|---|---|---|
| 5,540,921 A | * | 7/1996 | Tanaka | 424/401 |
| 6,660,491 B2 | * | 12/2003 | Norinobu et al. | 435/19 |
| 6,750,359 B1 | * | 6/2004 | Copeland et al. | 554/205 |

OTHER PUBLICATIONS

Abstract of JP 04108711A Apr. 1992.*

* cited by examiner

*Primary Examiner*—Eric E. Silverman
(74) *Attorney, Agent, or Firm*—Flynn, Thiel, Boutell & Tanis, P.C.

(57) ABSTRACT

A safe additive that increases the feeling effects from a hair cosmetic is provided at low costs. The additive that increases the feeling effects has less stickiness, can be easily and uniformly mixed with hair cosmetics, and can provide feelings, effects and advantages that are similar to those of sterol wax and lanolins including lanolin itself, liquid lanolin, and hard lanolin. The additive that increases the feeling effects contains a composition (I) prepared by distillation, fatty acid esterification, decoloring, and deodorization of a by-product obtained when tocopherol is extracted, separated and purified from a vegetable oil deodorized distillate.

7 Claims, 2 Drawing Sheets

VEGETABLE STEROL ESTER-CONTAINING COMPOSITION AND ADDITIVE THAT INCREASES THE FEELING EFFECTS FROM A HAIR COSMETIC

This is a division of Ser. No. 10/858,303, filed Jun. 1, 2004 now abandoned.

FIELD OF THE INVENTION

The present invention relates to a composition suitable for an ingredient of a hair cosmetic such as a hair setting agent, a hair conditioning agent, a finishing agent, a hair coloring agent and a waving agent. Furthermore, the present invention relates to a feeling improver of the hair cosmetic, i.e. an additive that increases the feeling effects of the hair cosmetic and that can provide excellent properties, effects and advantages.

DESCRIPTION OF THE PRIOR ART

Conventionally, lanolin (wool fat) has been used for various hair care products. For example, lanolin can provide hair and skin with a moist feeling, an adequate oily feeling and luster, and therefore is added to cosmetics, including hair cosmetics, emulsions, creams, lip sticks and lotions. Also, lanolin has excellent emulsification stability and emollient, and can be used as an emulsifying auxiliary agent, stabilizing agent and a softening agent.

However, lanolin has an original odor and a problem of being an allergen. In addition, animal-derived substances are generally unfavored because of health damages caused by the animal-derived substances such as BSE (bovine spongeform encephalopathy) in recent years.

Accordingly, attempts have been made to substitute non-animal-derived substances for lanolin. For example, Patent Document 1 describes an emulsifying agent comprising a plant sterol and a specific ester as a substitute for lanolin. Patent Document 2 describes a substitute for lanolin comprising an ethylene oxide adduct of a plant sterol, specific mixed esters and specific diglyceride.

However, all of the above-mentioned substitutes for lanolin contain synthetic materials. If the synthetic materials are orally or percutaneously absorbed, health problems may occur. In addition, the synthetic materials do not act mildly and are not benign to humans as compared with natural products.

On the other hand, as the non-animal-derived natural substances that are safe when human bodies absorb them, phytosterols (plant sterols) and phytosterol fatty acid esters are known. These substances are contained in plant foods including grains, vegetables, fruits and mushrooms, and are daily intaken from foods.

Cosmetics containing phytosterols and phytosterol fatty acid esters have been developed. Patent Document 3 describes a cosmetic containing phytosterol, hydrogenated phytosterol and a specific phytosterol fatty acid ester. Patent Document 4 describes a hair cosmetic containing, as effective ingredients, esters obtained from sterols such as stigmasterol and unsaturated fatty acids such as oleic acid.

However, none of the above-mentioned cosmetics has been developed as a substitute for lanolin. Accordingly, such cosmetics can not provide a moist feeling, an adequate oily feeling, and luster that are derived from lanolin.

Other cosmetics containing phytosterols and phytosterol fatty acid esters have been developed. Patent Document 5 discloses a cosmetic raw material as a substitute for lanolin comprising a steroid ester compound obtained from a hydroxyl aliphatic acid and phytosterol, and a specific alcohol ester. Patent Document 6 describes a cosmetic containing phytosterol or its derivative such as an oleic acid ester, a carboxyvinylpolymer, an alkyl-modified carboxyvinylpolymer and a specific silicone oil. Patent Document 7 describes a hair rinse composition containing a cationic surfactant, a higher alcohol, silicone and a specific oily agent such as phytosteryl oleate.

However, the above-mentioned cosmetics use phytosterols or phytosterol fatty acid esters that are obtained by preparing alone or separating, resulting in high costs from an industrial view point. Accordingly, the phytosterols or the phytosterol fatty acid esters are not suitable for use in cosmetics or a skin care preparation.

Patent Document 8 suggests a method of producing a plant sterol wax in good efficiencies and at low costs. The patent publication also suggests a skin care preparation containing a phytosterol, a phytosterol fatty acid ester and a plant sterol wax containing a hydrocarbon as a main ingredient. The skin care preparation gives a good feel in use and has stability.

As described above, the skin care preparation can be produced in good efficiencies and at low costs, and gives a good feel in use and is stable. In addition, the skin care preparation is prepared from a food vegetable oil such as soybean oil, and therefore is highly safe.

Patent document 1: Japanese Pat. Pub. No. 49-050140
Patent document 2: Japanese Pat. Pub. No. 58-198565
Patent document 3: Japanese Pat. Pub. No. 52-079030
Patent document 4: Japanese Pat. Pub. No. 02-0006404
Patent document 5: Japanese Pat. Pub. No. 09-194345
Patent document 6: Japanese Pat. Pub. No. 2002-145722
Patent document 7: Japanese Pat. Pub. No. 2001-139437
Patent document 8: Japanese Pat. Pub. No. 2001-163764

OBJECT OF THE INVENTION

Accordingly, it is an object of the present invention to provide a safe additive that increases the feeling effects from a hair cosmetic at low costs. The additive that increases the feeling effects has less stickiness, can be easily and uniformly mixed with hair cosmetics, and can provide feelings, effects and advantages that are similar to those of sterol wax and lanolins including lanolin itself, liquid lanolin and hard lanolin.

BRIEF SUMMARY OF THE INVENTION

In order to achieve the object, the present inventors carried out intensive research, and discovered that the use of a composition (I) containing a plant sterol ester is highly effective. The composition (I) is prepared by fatty acid esterification of a plant sterol wax as described below. The present invention is made based on the above-mentioned discovery.

The present invention provides a composition (I) prepared by distillation, fatty acid esterification, decoloring, and deodorization of a by-product obtained when tocopherol is extracted, separated and purified from a vegetable oil deodorized distillate.

Further, the present invention provides an additive that increases the feeling effects from a hair cosmetic comprising the above-mentioned composition (I) and a vegetable-derived fat and oil (II).

Preferably, the present invention provides an additive that increases the feeling effects from a hair cosmetic described-above, wherein the fat and oil (II) is a vegetable oil and/or a (partially) hydrogenated vegetable oil.

In the additive that increases the feeling effects from a hair cosmetic, when the fat and oil (II) is a vegetable oil and/or a (partially) hydrogenated vegetable oil, lanolin-like or hard lanolin-like feeling can be provided.

Another aspect of the present invention provides an additive that increases the feeling effects from a hair cosmetic further comprising a sucrose fatty acid ester (III) and a liquid higher fatty acid (IV).

In the additive that increases the feeling effects from a hair cosmetic, when the sucrose fatty acid ester (III) and the liquid higher fatty acid (IV) are added in addition to the composition (I) and the fat and oil (II), liquid lanolin-like feeling can be provided.

The present invention can provide a safe additive that increases the feeling effects from a hair cosmetic at low costs, an additive that increases the feeling effects having less stickiness, is capable of easily and uniformly mixing with hair cosmetics, and capable of providing feelings, effects and advantages—such as repair or protection of damaged hairs, and a moist feeling and an oily feeling similar to those provided by lanolin—those are similar to those of sterol wax and lanolins including lanolin itself, liquid lanolin and hard lanolin.

DESCRIPTION OF THE PREFERRED EMBODIMENT

The present invention will be described below in detail.

The additive that increases the feeling effects from the hair cosmetic of the present invention contains the composition (I) prepared by distillation, fatty acid esterification, decoloring, and deodorization of a by-product obtained when tocopherol is extracted, separated and purified from a vegetable oil deodorized distillate. The composition (I) can provide a sterol wax-like feeling. Polymer ingredients of the sterol wax contained in the composition (I) can repair and protect the damaged hair. The composition (I) can be produced at low costs, as compared with phytosterols or phytosterol fatty acid esters that are obtained by preparing alone (or by separating).

The vegetable oil deodorized distillate may be one distilled together with steam, when steam distillation is performed in the step of deodorizing the vegetable oil. Examples of the vegetable oil used as a raw material include food vegetable oil such as soybean, rapeseed, cotton seed, corn and sunflower.

In the preparation of the composition (I), a by-product (residual) obtained when tocopherol is extracted, separated and purified from the vegetable oil deodorized distillate is used. A method of extracting, separating and purifying tocopherol is, for example, as follows: The vegetable oil deodorized distillate is modified (esterification, non-saponification) if necessary, and tocopherol is then extracted with an organic solvent. Then, the extract is treated with a basic anion exchange resin and is adsorbed on the resin. Thereafter, the resin is passed through an organic solvent which contains an acid to elute and separate tocopherol from the resin, whereby purified tocopherol is provided.

Preferred examples of the methods are as follows:

1. A method of concentrating and purifying tocopherols by treating an alcohol extract of an esterified product or a non-saponified product of a tocopherol-containing substance at a low concentration, which is a by-product obtained in a purifying step of various vegetable oils and fats, with an OH basic anion ion exchange resin, and by passing the resin through an alcohol solution of boric acid as an extracting solvent to elute mixed tocopherols (Japanese Patent Application Publication No. 49-85222).

2. A method of purifying a tocopherol substance by preparing a solution of natural and synthesized tocopherol substances using a mono-alcohol having 1 to 4 carbon atoms, treating the solution with a basic anion exchange resin, adsorbing the tocopherol substances on the resin, and then eluting the tocopherol substances with a solution of formic acid, acetic acid or oxalic acid (Japanese Patent Examined Application Publication No. 38-23638).

3. A method of concentrating and purifying tocopherols by treating an aromatic hydrocarbon solution in which an esterified product or a non-saponified product of a tocopherol-containing substance are dissolved at a low concentration, which is a by-product obtained in a purifying step of various vegetable oils and fats, with an OH basic anion ion exchange resin, and by passing the resin through an alcohol solution of boric acid as an extracting solvent to elute mixed tocopherols (Japanese Patent Examined Application Publication No. 55-25189).

4. A method of purifying and concentrating tocopherols by dissolving tocopherol-containing substances in a solvent, passing the solution through a basic anion exchange resin to adsorb tocopherols on the resin, removing non-adsorbed impurities, and passing it through an extraction solution that has been treated with a carbonic acid gas to selectively elute the tocopherols (Japanese Patent Examined Application Publication No. 61-55917).

5. In a method of separating tocopherol from a tocopherol-containing substance at a low concentration, which is a by-product obtained in a purifying step of various vegetable oils and fats, by a methyl esterification reaction, a strong basic resin treatment of the reacted product, and elution of the tocopherol adsorbed on the resin, wherein (1) the methyl esterification reaction is performed in toluene, (2) a toluene layer of the reacted product of the methyl esterification reaction is treated with the strong basic resin as it is, and (3) the tocopherol adsorbed on the resin is eluted using toluene containing an acid as a developing solvent (Japanese Patent Examined Application Publication No. 61-57309).

Another example of the method of extracting, separating and purifying tocopherol from the vegetable oil deodorized distillate is to isolate the deodorized distillate from an esterified and distilled fraction. Detailedly, a method of separating tocopherols and sterols from a deodorant sludge by distilling the deodorant sludge, comprising the steps of: esterifying sterols in the deodorant sludge with a fatty acid therein prior to distillation, distilling the resultant mixture to provide a residual fatty acid and then the tocopherols, remaining sterol esters produced during the esterification within a distillation residual, isolating the tocopherols from the distillate, and isolating the sterols from the distillation residual after the sterol esters are cleaved (Japanese Patent No. 2648450).

According to the present invention, it is preferable that the free fatty acids contained in a deodorized distillate be esterified (i.e., methyl-esterified, ethyl-esterified) in an organic solvent such as toluene and xylene. Then, an organic solvent phase of the reacted product is treated with a strong basic anion exchange resin. Then, the resin is passed through a solution containing an acid, such as acetic acid and propionic acid, to separate the adsorbed tocopherol.

The composition (I) according to the present invention is prepared from a by-product, i.e., treated residual, which is provided during extraction, separation and purification of the tocopherol from the vegetable oil deodorized distillate. Accordingly, the composition (I) can be produced at very low costs.

When the strong basic anion exchange resin is used upon the separation and the purification of the tocopherol, the by-product generally contains sterols, sterol fatty acid esters, and hydrocarbons, which are ingredients not adsorbed on the strong basic anion exchange resin.

Upon the preparation of the composition (I) according to the present invention, it is preferable that the by-product obtained as described above be distilled to remove volatile ingredients such as fatty acid esters. The distillation may be performed at 150 to 160° C., preferably 152 to 158° C. and under 1 to 0.005 Torr, preferably 0.9 to 0.01 Torr.

Then, fatty acids are added to the distillation residual to change the ingredients such as phytosterols to fatty acid esters. The esterification of the fatty acid can prevent an oily feeling, and makes it easier to mix with other ingredients and hair cosmetics. In addition, the composition (I) can be easily purified, decolored, and deodorized in the subsequent steps to decrease the manufacturing costs. The fatty acids are preferably those contained in edible oils. Preferred examples of the fatty acids include C 16 to C 18 fatty acids, especially oleic acid, linoleic acid, and stearic acid. The fatty acids may be mixed in an amount of 60 to 120 parts by weight, preferably 80 to 100 parts by weight based on 500 parts by weight of the distillation residual. The esterification of the fatty acid may be conducted by applying heat, or agitating and mixing, if necessary.

Then, the esterified mixture is extracted, if necessary, and then decolored. The decoloring may be performed using an adsorbent such as active clay, acid clay and silica gel or an adsorbing resin such as Duolite XAD-761 and XAD-7.

The mixture is deodorized to provide the composition (I). Deodorization may be conducted by blowing water at 150 to 160° C., preferably 152 to 158° C. and under 10 to 0.1 Torr, preferably 8 to 0.5 Torr.

As an additive, an antioxidant such as δ-tocopherol and/or n-propyl gallate may be added to the composition (I).

The composition (I) prepared as described above comprises 3% by weight or less, typically 0.1 to 2.0% by weight of a free phytosterol such as stigmasterol, 55 to 65% by weight, typically 56.5 to 62% by weight of a phytosterol fatty acid ester such as phytosteryl oleate, 3 to 10% by weight, typically 6 to 8% by weight of triterpene alcohols such as trimethylsterol, 6 to 13% by weight, typically 2 to 5% by weight of hydrocarbons such as squalene and paraffin, and 3% by weight, typically 0.1 to 0.7% by weight of a fatty acid methyl ester.

The composition (I) has an acid value of 2.0 mg KOH/g or less, typically 1.0 to 1.7 mg KOH/g, a saponification value (measured by dissolving 2 g of a sample in 25 ml of xylene) of 60 to 95, typically 80 to 90, and an iodine value of 40 to 60 g $I_2$/100 g, typically 45 to 55 g $I_2$/100 g.

The additive that increases the feeling effects from a hair cosmetic of the present invention comprises a vegetable-derived fat and oil (II). A combination of the composition (I) and the fat and oil (II) can provide feelings, effects and advantages, especially moist and oily feelings, that are similar to those of lanolins.

Examples of the fat and oil (II) include vegetable oils and/or (partially) hydrogenated vegetable oils. Specific examples of the vegetable oils include rice germ oil, olive oil, safflower oil, soybean oil, sunflower seed oil, rapeseed oil, palm oil, jojoba oil, macadamia nut oil, castor oil, tsubaki oil, avocado oil, wheat germ oil and meadowfoam oil.

The (partially) hydrogenated vegetable oil is obtained by hardening and modifying, i.e., hydrogenating, at least a part of a vegetable oil. Specific examples of the (partially) hydrogenated vegetable oil include hydrogenated rice bran oil, partially hydrogenated bran oil, hydrogenated palm oil, partially hydrogenated palm oil, and hydrogenated soybean oil.

As an additive, higher alcohols such as C12 to C22 alcohols, esters such as C1 to C50 fatty acid esters and polybasic acid esters, and hydrocarbons may be added. These additives preferably have a high safety.

The additive that increases the feeling effects from a hair cosmetic of the present invention has generally a high safety, since it comprises the composition (I) and the fat and oil (II), both derived from vegetables.

Preferred embodiments of the additive that increases the feeling effects from a hair cosmetic of the present invention will be described below. One aspect of the present invention is an additive that increases the feeling effects from a hair cosmetic comprising the composition (I), and hydrogenated vegetable oil (II).

In this aspect, the hydrogenated vegetable oil is preferably hydrogenated rice bran oil and partially hydrogenated palm oil. As an additive, higher alcohols such as oleyl alcohol, esters such as dipentaerythritol fatty acid ester, and hydrocarbons such as paraffin may be added.

In this aspect, a combination of the composition (I) and the hydrogenated vegetable oil can provide an additive that increases the feeling effects from a hair cosmetic with a lanolin-like feeling. Specifically, the additive that increases the feeling effects can be a paste at room temperature that is in a similar form as lanolin. In addition, a lanolin-like feeling and functions including a moisture retention of hair, smoothness of hair, luster of hair, a rich taste of hair, wettability, emollient and protection of a hair can be provided. Moreover, excellent film-forming properties of hair can be provided.

In this aspect, the additive that increases the feeling effects comprises preferably 10 to 99% by weight, more preferably 70 to 95% by weight of the composition (I), and preferably 1 to 90% by weight, more preferably 5 to 30% by weight of the hydrogenated vegetable oil. If the additive that increases the feeling effects comprises less than 10% by weight of the composition (I), it may not provide enough film-forming properties and emollient. If the additive that increases the feeling effects comprises more than 95% by weight of the composition (I), the film-forming properties become too high to provide sufficient oily smoothness.

Another aspect of the present invention is an additive that increases the feeling effects from a hair cosmetic comprising the above-mentioned composition (I), and vegetable oil and (partially) hydrogenated vegetable oil (II).

In this aspect, the vegetable oil is preferably rice germ oil, macadamia nut oil and jojoba oil. The (partially) hydrogenated vegetable oil is preferably partially hydrogenated palm oil and hydrogenated rice bran oil. As an additive, higher alcohols such as oleyl alcohol, esters such as a dipentaerythritol fatty acid ester, and hydrocarbons such as paraffin may be added.

In this aspect, a combination of the composition (I), the vegetable oil and the (partially) hydrogenated vegetable oil can provide an additive that increases the feeling effects from a hair cosmetic with hard lanolin-like feeling. Specifically, the additive that increases the feeling effects can be a wax like a hard lanolin. In addition, a hard lanolin-like feeling including luster, film-forming properties, tension and stiffness can be provided. Moreover, smoothness can be provided to the hairs.

In this aspect, the additive that increases the feeling effects comprises preferably 10 to 70% by weight, more preferably 30 to 60% by weight of the composition (I), preferably 1 to 30% by weight, more preferably 5 to 15% by weight of the vegetable oil, and preferably 10 to 70% by weight, more preferably 30 to 60% by weight of the (partially) hydrogenated vegetable oil. If the additive that increases the feeling effects comprises less than 10% by weight of the composition (I), it may not provide enough film-forming properties and emollient. If the additive that increases the feeling effects comprises more than 95% by weight of the composition (I), sufficient tension and stiffness may not be provided. If the additive that increases the feeling effects comprises less than 1% by weight of the vegetable oil, it may not provide enough smoothness. If the additive that increases the feeling effects comprises more than 30% by weight of the vegetable oil, sufficient tension and stiffness may not be provided. If the additive that increases the feeling effects comprises less than 10% by weight of the (partially) hydrogenated vegetable oil, the film-forming properties are decreased, and sufficient tension and stiffness may not be provided.

Still another aspect of the present invention is an additive that increases the feeling effects from a hair cosmetic comprising the above-mentioned composition (I), and the vegetable oil as the compound (II).

In this aspect, the vegetable oil is preferably rice germ oil, olive oil, safflower oil, soybean oil, sunflower seed oil, rapeseed oil, palm oil, jojoba oil, macadamia nut oil, castor oil, tsubaki oil, avocado oil, wheat germ oil and meadowfoam oil. As an additive, higher alcohols such as oleyl alcohol, esters such as a dipentaerythritol fatty acid ester, and hydrocarbons such as paraffin may be added.

In this aspect, a combination of the composition (I) and the vegetable oil can provide an additive that increases the feeling effects from a hair cosmetic with a liquid lanolin-like feeling. Specifically, the additive that increases the feeling effects can be a liquid or paste similar to liquid lanolin. In addition, a liquid lanolin-like feeling and functions including smoothness of hair can be provided.

In this aspect, the additive that increases the feeling effects from a hair cosmetic preferably comprises a sucrose fatty acid ester (III) and a liquid higher fatty acid (IV) in addition to the composition (I) and the vegetable oil. The sucrose fatty acid ester (III) is preferably a full ester or a partial ester of sucrose and a C12 to C22 fatty acid such as sucrose hexaerucate, sucrose oleate, sucrose stearate, and sucrose palmitate. The "liquid" higher fatty acid has a flowability at room temperature, and can provide an additive that increases the feeling effects from a hair cosmetic with a liquid lanolin-like form. Examples of the liquid higher fatty acid include C16 to C22 fatty acids having a flowability at room temperature, especially oleic acid, linoleic acid, linolenic acid, and branched fatty acids such as isostearic acid. The branched fatty acids are especially preferable.

In this aspect, a combination of composition (I), the vegetable oil, the sucrose fatty acid ester and the liquid higher fatty acid can provide an additive that increases the feeling effects from a hair cosmetic with liquid lanolin-like properties. Specifically, the additive that increases the feeling effects can be similar to the liquid lanolin form. In addition, liquid lanolin-like feeling and functions can be provided. Especially, the sucrose fatty acid ester can provide emollient, a water-wrapping property, a moist feeling, a softening property, luster and moisture-retaining similar to liquid lanolin. The liquid higher fatty acid can provide hair smoothness.

In this aspect, the additive that increases the feeling effects comprises preferably 5 to 50% by weight, more preferably 20 to 40% by weight of the composition (I), preferably 10 to 90% by weight, more preferably 30 to 70% by weight of the vegetable oil, preferably 0.1 to 50% by weight, more preferably 1 to 20% by weight of the sucrose fatty acid ester and preferably 0.1 to 50% by weight, more preferably 1 to 20% by weight of the liquid higher fatty acid. If the additive that increases the feeling effects comprises less than 5% by weight of the composition (I), it less protects the hairs and may not provide enough emollient. If the additive that increases the feeling effects comprises more than 50% by weight of the composition (I), sufficient smoothness may not be provided. If the additive that increases the feeling effects comprises less than 10% by weight of the vegetable oil, it may not provide enough smoothness. If the additive that increases the feeling effects comprises more than 90% by weight of the vegetable oil, sufficient rich taste may not be provided. If the additive that increases the feeling effects comprises less than 0.1% by weight of the sucrose fatty acid ester, it may not provide enough emollient and moisture retention. If the additive that increases the feeling effects comprises more than 50% by weight of the sucrose fatty acid ester, the moist feeling may be too strong to decrease the smoothness. If the additive that increases the feeling effects comprises less than 0.1% by weight of the liquid higher fatty acid, it may decrease the smoothness. If the additive that increases the feeling effects comprises more than 50% by weight of the liquid higher fatty acid, sufficient emollient and protection may not be provided.

The additive that increases the feeling effects of the present invention can be mixed with any hair cosmetic such as a conditioner, a hair dressing agent, a rinse, a hair coloring agent, a waving agent, and a finishing agent. The additive that increases the feeling effects of the present invention may be mixed therewith in the amount of, for example, 1 to 5% by weight.

EXAMPLES

The examples which follow are illustrative of the present invention and are not intended to be limiting in any way.

Preparation of the Composition (I)

Preparation Example 1

2000 g of a deodorized distillate (total tocopherol content of 10.3%, acid value of 81) obtained by deodorizing soybean oil as a by-product was methyl-esterified in a mixed solvent of 100 ml of methanol and 1000 ml of toluene in the presence of 130 g of sulfuric acid under reflux for 1 hour. An oily substance was separated, and washed four times with 500 ml of water. The acid value was 1 after the methyl-esterification. The resultant product was cooled to room temperature, and deposited crystals were filtered and separated. 8.9 g of the crystals were removed by the filtration.

A column was filled with 2000 ml of a strong basic anion exchange resin, "Amberlite IRA958" to be an OH type, which was then replaced with toluene. Then, a solution of the prepared methyl-esterified oil in toluene was passed therethrough. 4000 ml of toluene flowed through the column to wash the resin and then was removed to provide 1670 g of non-adsorbed oil. The tocopherol adsorbed was eluted by flowing 4000 ml of 10% methanol acetate to provide 257 g of tocopherol concentrated oil.

A fatty acid methyl ester contained in the non-adsorbed oil was removed by reduced distillation. To 500 g of the residual, 80 g of oleic acid was added, and reacted under a nitrogen atmosphere at 200° C. for 24 hours. Five liters of hexane was added to the reacted mixture, and stirred and dissolved. Two liters of 80% methanol aqueous solution to which 10 g of sodium hydroxide has been added were added to remove excess oleic acid. The hexane layer was washed with 2 liters of 70% methanol aq. solution four times and then 3 liters of water four times. 45 g of active clay and 30 g of active carbon were added thereto and stirred under reflux for 1 hour. The resultant product was cooled to room temperature, filtered and concentrated.

0.44 g of δ-tocopherol and 0.06 g of propyl gallate were added to the concentrated liquid. 30 ml of water was blown thereto at a degree of vacuum of 10 to 0.1 Torr and at 150 to 160° C. for 2 hours. By these operations, 487 g of paste-like oil having a pale yellow color to a pale brown color was obtained. The oil had an acid value of 0.8 and a saponification value of 83.7, and was analyzed by gas chromatography. As a result, it included 1.7% of a sterol, 61.0% of a sterol fatty acid ester and 7.3% of a hydrocarbon.

Preparation Example 2

2000 g of a deodorized distillate (total tocopherol content of 9.8%, acid value of 78) obtained by deodorizing vegetable oil (a 1:1 mixture of soybean oil and rapeseed oil) as a by-product was methyl-esterificated in a mixed solvent of 1000 ml of methanol and 1000 ml of toluene in the presence of 130 g of sulfuric acid under reflux for 1 hour. An oily substance was separated, and washed four times with 500 ml of water. The acid value was 1 after the methyl-esterification. The resultant product was cooled to room temperature, and deposited crystals were filtered and separated. 9.2 g of the crystals were removed by the filtration.

A column was filled with 2000 ml of a strong basic anion exchange resin, "Duolite A113", an OH type, which was then replaced with toluene. Then, a solution of the prepared methyl-esterificated oil in toluene was passed therethrough. 4000 ml of toluene flowed through the column to wash the resin, and was removed to provide 1650 g of non-adsorbed oil. The tocopherol adsorbed was eluted by flowing 4000 ml of 10% methanol acetate to provide 248 g of tocopherol concentrated oil.

A fatty acid methyl ester contained in the non-adsorbed oil was removed by reduced distillation. To 510 g of the residual, 82 g of oleic acid and 20 g of linoleic acid was added, and reacted under a nitrogen atmosphere at 200° C. for 24 hours. Five liters of hexane was added to the reacted mixture, and stirred and dissolved. Two liters of 80% methanol aq. solution to which 10 g of sodium hydroxide has been added were added to remove excess oleic acid and linoleic acid. The hexane layer was washed with 2 liters of 70% methanol aq. solution four times and then 3 liters of water four times. 45 g of active clay and 30 g of active carbon were added thereto and stirred under reflux for 1 hour. The resultant product was cooled to room temperature, filtered and concentrated. 30 ml of water was blown thereto at a degree of vacuum of 10 to 0.1 Torr and at 150 to 160° C. for 2 hours. By these operations, 504 g of a paste-like oil having a pale yellow color to a pale brown color was obtained. The oil had an acid value of 0.1 and a saponification value of 74.8, and was analyzed by gas chromatography. As a result, it included 1.9% of a sterol, 62.1% of a sterol fatty acid ester and 9.0% of a hydrocarbon.

GPC Analysis and Capillary GC Analysis of the Composition (I)

Figure 1:
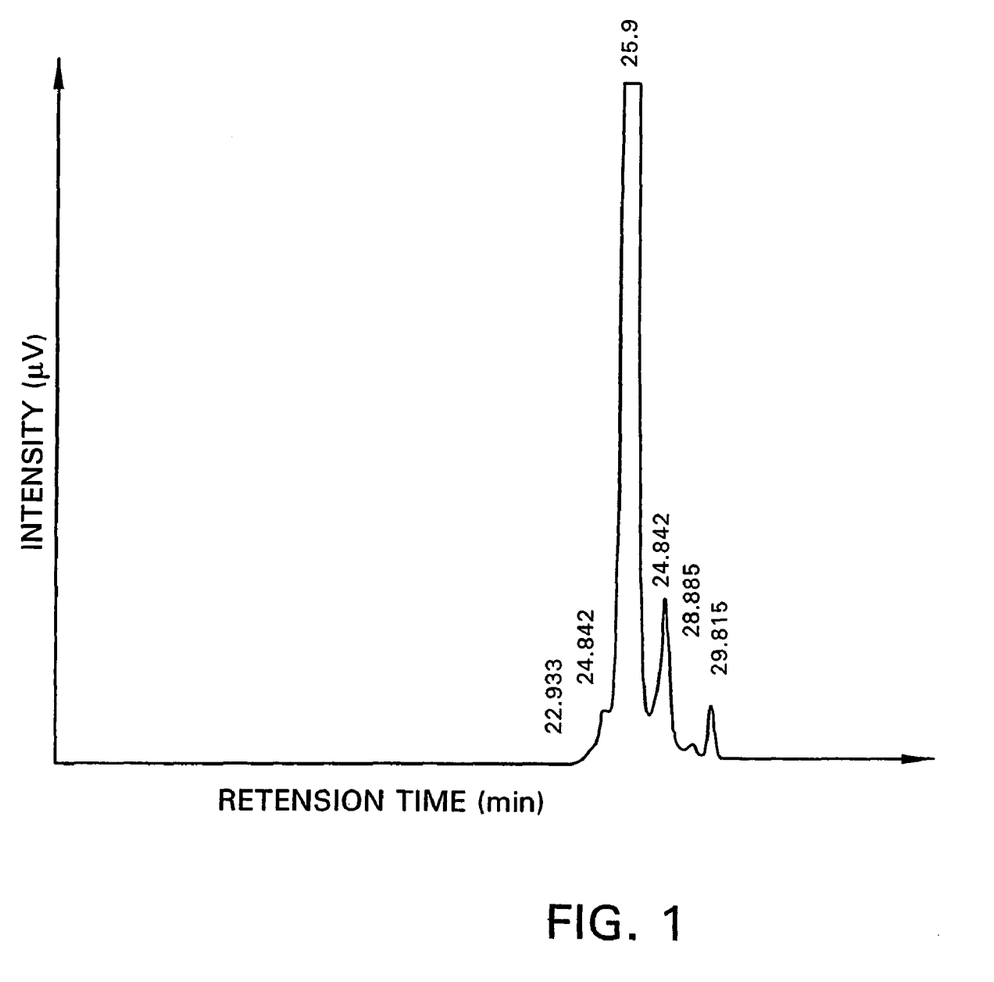
FIG. 1 is a GPC analysis chart of Preparation Example 1.
Figure 2:
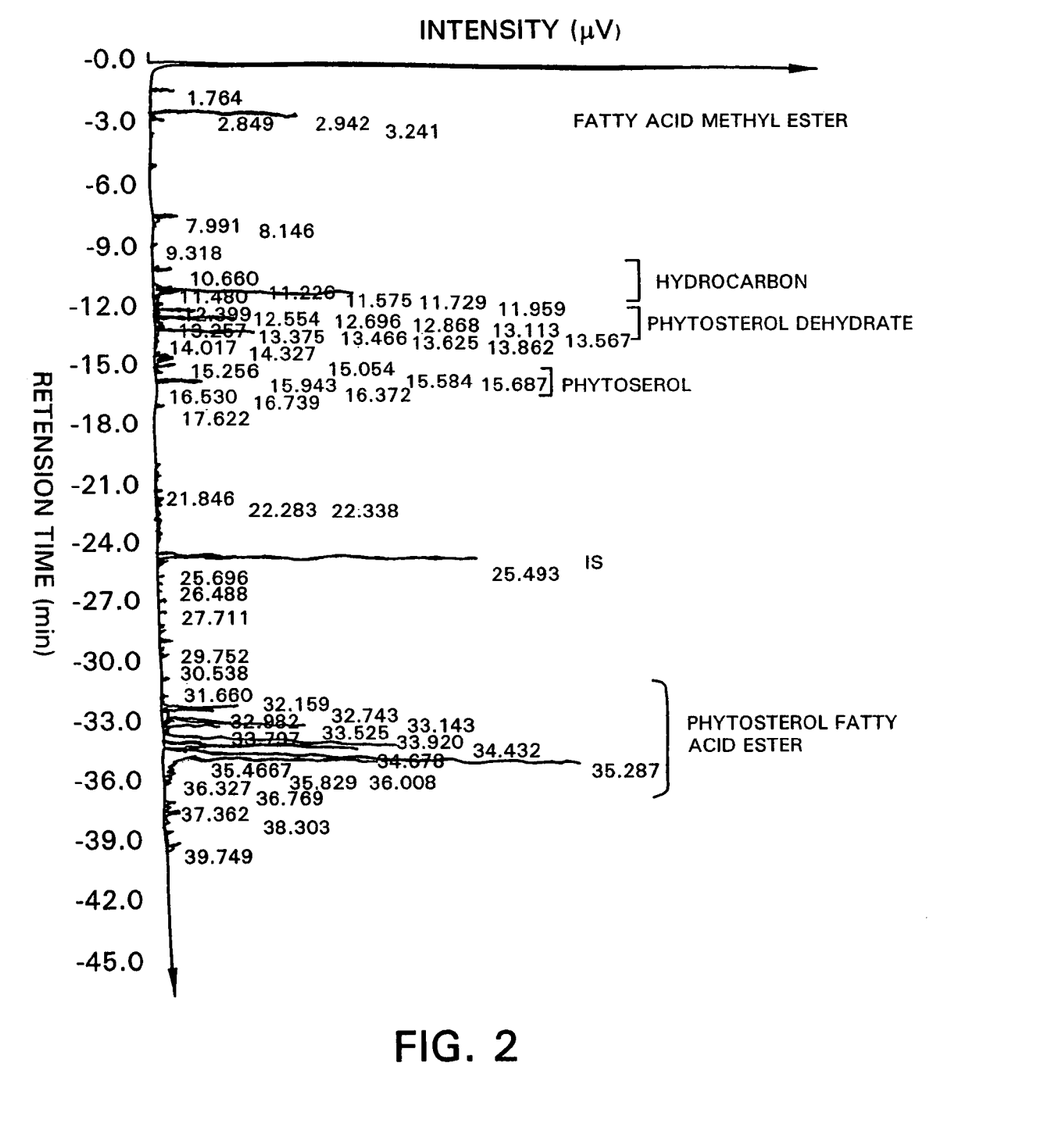
FIG. 2 is a GC analysis chart of Preparation Example 2.

A GPC analysis of preparation example 1 and a GC analysis of preparation example 2 were performed using the following measurement conditions and methods. FIGS. 1 and 2 are charts showing respectively the measurement results of A GPC analysis of preparation example 1 and a GC analysis of preparation example 2. The names of compounds are written at corresponding peaks in the charts.

(GPC Analysis)

Preparation of a Standard Solution 10 to 25 mg of each standard substance shown in Table 1 was precisely weighed in a 50 ml measuring flask, chloroform was added and dissolved to be 50 ml, whereby each standard solution was thus prepared.

TABLE 1

| Ingredient | Standard substance | Manufacturer (No.) |
|---|---|---|
| fatty acid methyl ester | methyl oleate | Wako Pure Chemical Industries, Ltd. (133-08581) |
| phytosterol | stigmasterol | Tama Biochemical Co., Ltd |
| phytosterol fatty acid ester | cholesteryl oleate | ICN (100443) |
| phytosterol dehydrate | stigmaster-3,5-diene | synthetic material |
| squalene | squalene | Wako Pure Chemical Industries, Ltd. (198-09735) |
| paraffin | C-27(n-heptacosane) | Tokyo Kasei Kogyo Co., Ltd. (H0017) |

Preparation of Sample Solution 200 mg of a sample substance (preparation example 1) was precisely weighed in a 50 ml measuring flask, toluene was added and dissolved to be 50 ml, whereby a sample solution was thus prepared.

GPC Analysis Conditions

Column: K-801 (made by Shodex, exclusion limit molecular weight; 1500)

K-802 (made by Shodex, exclusion limit molecular weight; 5000)

Eluent: chloroform

Flow rate: 0.5 ml/min

Temperature: 35° C.

Detection: light scattering detector (GAS1.0 NEB.40° C. EVA.80° C.)

GPC Analysis Method

20 μl of the standard solution and 20 μl of the sample solution were fed into the columns under the above-mentioned conditions. Retention times of respective standard substances were determined from analyzing the charts of the respective standard solutions. The retention times of the standard substances at respective peaks were collated with those of ingredients at respective peaks contained in the sample solution. By collating the peaks, the ingredients contained in the sample solution were determined. Area percentage ratios of respective peaks corresponded to the concentrations of the respective ingredients at the respective peaks.

Table 2 shows the main ingredients and their concentrations between the retention times of about 20 to 30 minutes shown in the GPC chart of FIG. 1.

TABLE 2

| PK No. | retention time (min) | main ingredient | concentration (wt %) |
|---|---|---|---|
| 1 | 22.833 | polymer ingredient | 0.0034 |
| 2 | 24.842 | | 1.7941 |
| 3 | 25.9 | sterol esters | 91.5047 |
| 4 | 27.7 | hydrocarbons | 5.1065 |
| 5 | 28.885 | sterols | 0.4522 |
| 6 | 29.815 | hydrocarbons | 1.139 |

(GC Analysis)

Preparation of Internal Standard Solution 25 mg of cholesteryl n-decylate (SIGMA; C-4633) was precisely weighed in a 50 ml measuring flask, 20 ml of hexane was added, heated and dissolved. While cooling to room temperature, chloroform was added to be 50 ml.

Preparation of Standard Solution 10 to 25 mg of each standard substance shown in Table 1 was precisely weighed in a 50 ml measuring flask, toluene was added and dissolved to be 50 ml. 5 ml of the resultant solution was taken out to a 25 ml screw vial. 5 ml of the internal standard solution was added thereto, whereby each standard solution was thus prepared.

Preparation of Sample Solution 200 mg of a sample substance (preparation example 2) was precisely weighed in a 50 ml measuring flask, toluene was added and dissolved to be 50 ml, 5 ml of the resultant solution was taken out to a 25 ml screw vial. 5 ml of the internal standard solution was added thereto, whereby a sample solution was thus prepared.

GC Analysis Conditions

Device: GC-17A

Column: DB-1HT (made by J&W Scientific, 15 m, 0.25 mm I.D., 0.10 μm film thickness)

Carrier gas: He 92 kPa

Temperature increase program: 150 to 250° C. (5° C./min)+ 250 to 350° C. (10° C./min)

Feeding method: split method (split ratio of 45:1, at 350° C.)

Detector: FID (at 350° C.)

GC Analysis Method

2 μL of the standard solution and 2 μL of the sample solution were fed into the device under the above-mentioned conditions. An area of the phytosterol was calculated by adding four peaks: brassicasterol, campesterol, stigmasterol and sitosterol. An area of phytosterol fatty acid ester was calculated by adding four peaks of sterol-derived C16 fatty acid esters and four peaks of sterol-derived C18 fatty acid esters. Areas of the hydrocarbons were calculated by adding peaks of squalene and paraffin. The resultant areas and the weights upon the solution preparation are applied to the following equations to calculate the concentration of the respective ingredients in the sample.

[Concentration (%)]=[(area of sample)/(area of internal standard solution)]×[(amount of internal standard solution (mg))/(amount of sample (mg))]× (correction factor)×100

[Correction factor]=[(amount of standard solution (mg))/(amount of internal standard solution (mg))]×[(area of internal standard solution)/(area of standard solution)]

Preparation of Vegetable Sterol Wax

Comparative Preparation Example 1

About 1700 g of a by-product obtained by extracting, separating and purifying tocopherol from a vegetable oil deodorized distillate was fed into a distiller, and distilled under about 1.0 to 0.001 Torr at about 150 to 160° C. to provide about 1120 g of a fatty acid ester fraction. About 2300 ml of hexane was added to the distillation residual and stirred. After the portions not dissolved were filtered and removed, about 60 g of active clay was added and stirred for 30 minutes. The resultant mixture was filtered and concentrated. Then, about 30 ml of water was blown thereinto under about 10 to 0.1 Torr and at about 150 to 160° C. for 2 hours. By these operations, about 550 g of a paste-like oil (vegetable sterol wax) having a pale yellow color to a pale brown color was obtained. The oil had an acid value of about 0.3 and a saponification value of about 48.5, and contained about 19% of a sterol, about 41% of a sterol fatty acid ester and about 16% of a hydrocarbon.

Preparation of Additive that Increases the Feeling Effects from a Hair Cosmetic

Examples 1 to 10 and Comparative Examples 1 to 3

In accordance with the formulations shown in Tables 3 and 4, respective ingredients were heated at about 80° C., if necessary, dissolved, stirred and mixed uniformly to prepare respective additives that increase the feeling effects.

Various Evaluation Test Results of the Additives that Increase the Feeling Effects The respective additives that increase the feeling effects in Examples 1 to 10 and Comparative Examples 1 to 3 were used to prepare hair conditioners including the formulations as described below. The hair conditioners containing the respective additives that increase the feeling effects were applied to hairs after shampooing, spread by combing, rinsed and dried with a dryer. The organoleptic tests were conducted by plural panelists. Tables 3 and 4 show the results. The production costs were evaluated based on the purchase prices of the raw materials.

Formulation (% by Weight) of Hair Conditioner Containing an Additive that Increases the Feeling Effects:

cetanol 5, isopropyl myristate 1, cetyl trimethyl ammonium chloride 2, lipophilic glyceryl monosterarate 1, dimethyl polysiloxane (containing a high polymer) 3, paraffin 0.5, glycerin 3.5, an additive that increases the feeling effects 3 and purified water, residual.

TABLE 3

| | | Examples | | | | | | |
|---|---|---|---|---|---|---|---|---|
| | | 1 | 2 | 3 | 4 | 5 | 6 | 7 |
| Ingredient (weight %) | composition (I) in preparation example 1 | 90 | 40 | 40 | 40 | 40 | 35 | 30 |
| | vegetable wax of comparative preparation 1 | — | — | — | — | — | — | — |
| | phytosteryl oleate | — | — | — | — | — | — | — |
| | hydrogenated rice bran oil | 10 | 50 | — | — | — | — | — |
| | palm partial hardened oil | — | — | 50 | 50 | — | — | — |
| | rice germ oil | — | — | — | 10 | 60 | 60 | 60 |
| | macadamia nut oil | — | 10 | — | — | — | — | — |
| | castor oil | — | — | 10 | — | — | — | — |

TABLE 3-continued

|  |  | Examples |  |  |  |  |  |  |
|---|---|---|---|---|---|---|---|---|
|  |  | 1 | 2 | 3 | 4 | 5 | 6 | 7 |
| Ingredient (weight %) | sucrose hexaerucate | — | — | — | — | — | — | 10 |
|  | oleic acid sucrose | — | — | — | — | — | — | — |
|  | isostearic acid | — | — | — | — | — | 5 | — |
|  | isostearyl alcohol | — | — | — | — | — | — | — |
| Evaluation test results | less stickiness | ○ | ◎ | ◎ | ◎ | ○ | ◎ | ○ |
|  | uniform mixing property with hair cosmetic | ○ | ○ | ○ | ○ | ○ | ○ | ○ |
|  | hair repair and protection properties | ◎ | ◎ | ◎ | ◎ | ○ | ○ | ○ |
|  | hair moist feeling | ○ | ○ | ○ | ○ | ○ | ○ | ◎ |
|  | hair oily feeling | ◎ | ◎ | ◎ | ◎ | ○ | ○ | ○ |
|  | hair smoothness | ○ | ◎ | ◎ | ◎ | △ | ◎ | △ |
|  | hair tension and stiffness | ○ | ◎ | ◎ | ◎ | △ | △ | ○ |
|  | moisture-retaining functions of hair | ○ | ○ | ○ | ○ | ○ | ○ | ◎ |
|  | hair coating feeling | ◎ | ◎ | ◎ | ◎ | ○ | ○ | ○ |
|  | hair rich taste | ◎ | ◎ | ◎ | ◎ | ○ | ○ | ○ |
|  | water-wrapping property | ○ | ○ | ○ | ○ | ○ | ◎ | ◎ |
|  | low production costs | ◎ | ◎ | ◎ | ◎ | ◎ | ◎ | ◎ |

TABLE 4

|  |  | Examples | | | Comparative Examples | | |
|---|---|---|---|---|---|---|---|
|  |  | 8 | 9 | 10 | 1 | 2 | 3 |
| Ingredient (weight %) | composition (I) in preparation example 1 | 25 | 25 | 25 | 100 | — | — |
|  | vegetable wax of comparative preparation 1 | — | — | — | — | 90 | — |
|  | phytosteryl oleate | — | — | — | — | — | 90 |
|  | hydrogenated rice bran oil | — | — | — | — | 10 | 10 |
|  | palm partial hardened oil | — | — | — | — | — | — |
|  | rice germ oil | 60 | 60 | 60 | — | — | — |
|  | macadamia nut oil | — | — | — | — | — | — |
|  | castor oil | — | — | — | — | — | — |
|  | sucrose hexaerucate | 10 | 10 | — | — | — | — |
|  | oleic acid sucrose | — | — | 10 | — | — | — |
|  | isostearic acid | — | 5 | 5 | — | — | — |
|  | isostearyl alcohol | 5 | — | — | — | — | — |
| Evaluation test results | less stickiness | ◎ | ◎ | ◎ | ○ | △ | ◎ |
|  | uniform mixing property with hair cosmetic | ◎ | ◎ | ◎ | ○ | △ | ○ |
|  | hair repair and protection properties | ○ | ○ | ○ | ◎ | ○ | △ |
|  | hair moist feeling | ◎ | ◎ | ◎ | △ | ◎ | ○ |
|  | hair oily feeling | ○ | ○ | ○ | △ | ○ | ○ |
|  | hair smoothness | △ | ◎ | ◎ | △ | △ | ○ |
|  | hair tension and stiffness | ○ | ○ | ○ | ○ | ○ | △ |
|  | moisture-retaining functions of hair | ◎ | ◎ | ◎ | ○ | ○ | ○ |
|  | hair coating feeling | ○ | ○ | ○ | ○ | ○ | △ |
|  | hair rich taste | ○ | ○ | ○ | ○ | ○ | ○ |
|  | water-wrapping property | ◎ | ◎ | ◎ | ○ | ○ | ○ |
|  | low production costs | ◎ | ◎ | ◎ | ◎ | ○ | X |

In tables,
◎ represents "superior",
○ represents "excellent",
△ represents "fair" and
X represents "poor."

The data in Tables 3 and 4 show that the hair conditioners containing the additives that increase the feeling effects according to the present invention (Examples 1 to 10) had less stickiness, and the additives that increase the feeling effects according to the present invention (Examples 1 to 10) can be easily and uniformly mixed with hair cosmetics, provide feelings, effects and advantages including hair moist and oily feelings that are similar to those of a sterol wax and lanolins including lanolin itself, liquid lanolin and hard lanolin and be manufactured at a low cost.

In particular, the additive that increases the feeling effects comprising the composition (I) and the hydrogenated vegetable oil as the ingredient (II) in Example 1 provided excellent hair coating feeling (or film-formed hair feeling) and hair rich taste like lanolin.

In addition, the additives that increase the feeling effects comprising the composition (I), the vegetable oil and the (partially) hydrogenated vegetable oil as the ingredient (II) in each Examples 2 to 4 provided excellent hair smoothness, tension and stiffness of hair, coating feeling and hair rich taste like hard lanolin.

Moreover, the additives that increase the feeling effects each comprising the composition (I), the vegetable oil as the ingredient (II), the sucrose fatty acid ester (III) and the liquid higher fatty acid (IV) in Examples 9 and 10 provided excellent hair smoothness, moisture retention and water-wrapping property like liquid lanolin.

On the other hand, the hair conditioner containing no ingredient (II) in Comparative Example 1 provided decreased lanolin-like feelings including hair moist feeling, oily feeling and smoothness.

The hair conditioner containing the vegetable sterol wax instead of the composition (I) in Comparative Example 2, in comparison with the hair conditioner using the composition (I), provided increased stickiness, and decreased uniform mixing property with the hair cosmetics, and increased the production costs because of the decrease of the easiness of the isolation and purification of the vegetable sterol wax.

The hair conditioner containing phytosteryl oleate instead of the composition (I) in Comparative Example 3 provided poor hair repair and protection properties, poor hair tension and stiffness, and poor coated (or filmed) feeling. Further, because the phytosteryl oleate is expensive, the production costs increases.

Preparation of Raw Materials for Hair Conditioner
    Preparation of Raw Materials 1, 2, 4 to 6, 8, 9 to 17
    Respective ingredients were mixed and stirred uniformly to prepare the raw materials. Tables 5 and 6 show the formulations.
    Preparation of Raw Materials 3 and 7
    After respective oily ingredients other than an anion surfactant were mixed and stirred uniformly, the anion surfactant and aqueous ingredients were added gradually thereto, mixed and stirred uniformly to prepare the raw materials. Table 5 shows the formulations.

TABLE 5

| Ingredient (wt %) | Base material 1 | 2 | 3 | 4 | 5 | 6 | 7 | 8 |
|---|---|---|---|---|---|---|---|---|
| composition (I) in preparation example 1 | 10 | 4 | 1.9 | — | 18.52 | — | — | — |
| myristyl alcohol | — | — | 24.3 | — | — | — | — | — |
| cetanol | 30 | — | — | — | — | — | — | 30 |
| oleyl alcohol | 1 | — | — | — | 3.7 | — | — | 1 |
| behenyl alcohol | 14 | — | 26.2 | 56.2 | — | — | 21 | 14 |
| cetostearyl alcohol | — | 36 | — | — | — | — | — | — |
| stearyl alcohol | — | — | — | — | — | 21 | 43 | — |
| stearyl trimethyl ammonium chloride | — | 24 | — | — | — | — | — | — |
| behenyl trimethyl ammonium chloride | 10 | — | — | — | — | — | — | 10 |
| cethyl trimethyl ammonium bromide | 20 | — | — | — | — | — | — | 20 |
| alkyl (C16, C18 mix.) trimethyl ammonium chloride | — | — | — | — | 55.56 | 35.3 | — | — |
| sodium cocoyl ethyl ester sulfonate | — | — | 19.4 | — | — | — | — | — |
| sodium palmitoyl N-metyl taurate | — | — | — | — | — | — | 14 | — |
| stearic acid dimethyl amino propyl amide | — | — | — | 18 | — | — | — | — |
| jojoba oil | 3 | — | — | — | — | — | — | 3 |
| rice bran oil | — | — | — | — | 3.7 | — | — | — |
| hydrogenated rice germ oil | 5 | — | 9.7 | — | — | — | — | 5 |
| palm partial hardened oil | — | — | — | — | 9.26 | — | — | — |
| isopropyl myristate | 2 | — | — | — | — | — | — | 2 |
| isopropyl palmitate | — | — | — | — | — | 3 | — | — |
| hexyldecyl isostearate | — | 4 | — | 15.7 | — | — | — | — |
| glyceryl monomyristate | — | — | 7.8 | — | — | — | — | — |
| glyceryl monostearate | 5 | — | — | 10.1 | 9.26 | 36 | 7 | 5 |
| polyethylene glycol monostearate(25EO) | — | — | — | — | — | — | 5 | — |
| light liquid isoparaffin | — | 32 | — | — | — | — | — | — |
| [triethanolamine N-cocoyl-L-glutamate (30%) + water(70%)]mix. | — | — | 7.8 | — | — | — | — | — |
| purified water | — | — | residual | — | — | — | residual | — |
| POE(15EO) cetyl ether | — | — | — | — | — | 4.7 | 4.5 | — |

TABLE 6

| Ingredient (wt %) | Base 9 | 10 | 11 | 12 | 13 | 14 | 15 | 16 | 17 |
|---|---|---|---|---|---|---|---|---|---|
| composition (I) in preparation example 1 | 25 | — | — | 90 | — | — | 40 | — | — |
| vegetable wax | — | 25 | — | — | 90 | — | — | 40 | — |
| phytosteryl oleate | — | — | 25 | — | — | 90 | — | — | 40 |
| rice bran oil | 60 | 60 | 60 | — | — | — | 10 | 10 | 10 |
| hydrogenated rice germ oil | — | — | — | 10 | 10 | 10 | — | — | — |
| palm partial hardened oil | — | — | — | — | — | — | 50 | 50 | 50 |
| sucrose hexaerucate | 10 | 10 | 10 | — | — | — | — | — | — |
| isostearic acid | 5 | 5 | 5 | — | — | — | — | — | — |

Preparation of Hair Conditioners

Samples 1 to 27, Comparative Samples 1 to 17 and Controls 1 to 9

Respective oily ingredients were mixed and stirred uniformly by, if necessary, heating at about 80° C. Respective aqueous ingredients were mixed and stirred uniformly by, if necessary, heating at about 80° C. The aqueous mixture was gradually added to the oily mixture. The combined mixture was cooled, adjusted by adding water and mixed and stirred uniformly to prepare the hair conditioners of Samples 1 to 27, Comparative Samples 1 to 17 and Controls 1 to 9. Tables 7 to 10 show the formulations.

In Samples 9 to 27 and Comparative Samples 5 to 17, two types of bases were added. "Highly polymerized polyethylene glycol" has a number average molecular weight of two million. The highly polymerized polyethylene glycol used in the percentage shown in each Table was dissolved in water to be a 2% solution.

In Table 7, suffixes 1) to 5) are as follows:
1) average molecular weight of 1200
2) composition A: highly polymerized methyl polysiloxane (13 wt %)+an aminoethyl aminopropyl methylsiloxane–dimethylsiloxane copolymer (15 wt %)+methylpolysiloxane (72 wt %)
3) composition B: highly polymerized methyl polysiloxane (100,000 cs, 30 wt %)+highly polymerized methyl polysiloxane (10,000 cs, 20 wt %)+methyl polysiloxane (20 cs, 50 wt %)
4) composition C: trimethyl glycine (40 wt %)+a 8% solution of a dimethyl diallyl ammonium chloride–acrylamide copolymer+D-mannitol (4 wt %)+methyl parahydroxybenzoate (0.1 wt %)+ethanol (2 wt %)+purified water (residual)
5) composition D: [a polyvinylpyrrolidone–vinyl caprolactam–dimethyl aminopropyl methacrylamide copolymer+ethanol (weight ratio of 4:6)] mixture (50 wt %)+1,3-butylene glycol (50 wt %)

Various Evaluation Test Results of the Hair Conditioners

The hair conditioners were applied to hairs after shampooing, spread by combing, rinsed and dried with a dryer to provide test hairs. The organoleptic tests were conducted by plural panelists.

"Hair repair and protection properties" were evaluated by plural panelists whose hairs were treated with a hair coloring agent, a bleaching agent or a permanent waving agent three times, and then were applied the hair conditioner. "Production costs" were evaluated based on the purchase prices of the raw materials. An "unpleasant creaky feeling upon rinsing" was determined by touching the test hairs upon the shampooing.

Tables 7 to 10 show the results. In "less stickiness" and "unpleasant creaky feeling upon rinsing" evaluations, ⊚ represents "almost nothing," ○ represents "some," Δ represents "fair," and x represents "much." In "emollient" and "hair repair and protection properties" evaluations, ⊚ represents "superior," ○ represents "excellent," Δ represents "fair," and x represents "poor." In "low production costs" evaluations, ⊚ represents "very low," ○ represents "low," Δ represents "fair," and x represents. "very high." In "hair smoothness," "hair luster," "hair rich taste," "hair film-forming properties," and "hair tension and stiffness," ⊚ represents "excellent similar to or better than controls," ○ represents "better than the hair conditioners containing no lanolins, but poor as compared with controls," and Δ represents "similar to the hair conditioners containing no lanolins."

TABLE 7

| | | | Sample | | | | | | | |
|---|---|---|---|---|---|---|---|---|---|---|
| | | | 1 | 2 | 3 | 4 | 5 | 6 | 7 | 8 |
| Ingredient (wt %) | base | (No.) | 1 | 1 | 2 | 3 | 7 | 7 | 4 | 4 |
| | | (cotent) | 10 | 10 | 12.5 | 12 | 14 | 14 | 10 | 10 |
| | composition (I) in preparation example 1 | | — | — | — | — | 1 | 1 | 5 | 5 |
| | vegetable wax | | — | — | — | — | — | — | — | — |
| | phytosteryl oleate | | — | — | — | — | — | — | — | — |
| | stearyl trimethyl ammonium bromide | | — | — | 0.4 | — | — | — | — | — |
| | 90% lactic acid | | — | — | — | — | — | — | 0.66 | 0.66 |
| | isononyl isononanoate | | — | — | 0.4 | — | — | — | — | — |
| | POE(12EO) secondary alkyl (C12 to C14 mix.) ether | | — | — | 0.2 | — | — | — | — | — |
| | white vaseline | | — | — | — | 0.5 | | | — | — |
| | [N-{2-hydroxy-3-(trimethylammonio) propyl chloride} hydrolyzed keratin[1] (25%) + purified water (75%)] mix. | | — | — | 1 | — | | | — | — |
| | composition A[2] | | — | — | 1 | — | — | — | — | — |
| | composition B[3] | | — | — | 3.5 | — | — | — | — | — |
| | composition C[4] | | — | — | 8 | — | — | — | — | — |
| | composition D[5] | | — | — | — | 5 | — | — | — | — |
| | highly polymerized polyethylene glycol | | — | 0.02 | — | — | — | 0.02 | — | 0.02 |
| | methylparaben | | 0.1 | 0.1 | 0.1 | 0.1 | 0.1 | 0.1 | 0.3 | 0.3 |
| | propylparaben | | 0.05 | 0.05 | 0.05 | 0.05 | 0.05 | 0.05 | 0.1 | 0.1 |
| | purified water | | residual | residual | residual | residual | residual | residual | residual | residual |
| Evaluation test results | less stickiness | | ⊚ | ⊚ | ⊚ | ⊚ | ⊚ | ⊚ | ⊚ | ⊚ |
| | emollient | | ⊚ | ⊚ | ⊚ | ⊚ | ⊚ | ⊚ | ⊚ | ⊚ |
| | hair repair and protection properties | | ⊚ | ⊚ | ⊚ | ⊚ | ⊚ | ⊚ | ⊚ | ⊚ |
| | low production costs | | ⊚ | ⊚ | ⊚ | ⊚ | ⊚ | ⊚ | ⊚ | ⊚ |
| | unpleasant creaky feeling upon rinsing | | ⊚ | ⊚ | ⊚ | ○ | Δ | ⊚ | Δ | ⊚ |

| | | | Comparative Sample | | | |
|---|---|---|---|---|---|---|
| | | | 1 | 2 | 3 | 4 |
| Ingredient (wt %) | base | (No.) | 8 | 8 | 7 | 4 |
| | | (cotent) | 9 | 9 | 14 | 10 |
| | composition (I) in preparation example 1 | | — | — | — | — |
| | vegetable wax | | 1 | — | — | 5 |
| | phytosteryl oleate | | — | 1 | 1 | — |
| | stearyl trimethyl ammonium bromide | | — | — | — | — |
| | 90% lactic acid | | — | — | — | 0.66 |
| | isononyl isononanoate | | — | — | — | — |
| | POE(12 EO) secondary alkyl (C12 to C14 mix.) ether | | — | — | — | — |
| | white vaseline | | — | — | — | — |
| | [N-{2-hydroxy-3-(trimethylammonio) propyl chloride} hydrolyzed keratin[1] (25%) + purified water (75%)] mix. | | — | — | — | — |
| | composition A[2] | | — | — | — | — |
| | composition B[3] | | — | — | — | — |
| | composition C[4] | | — | — | — | — |
| | composition D[5] | | — | — | — | — |
| | highly polymerized polyethylene glycol | | — | — | — | — |
| | methylparaben | | 0.1 | 0.1 | 0.1 | 0.3 |
| | propylparaben | | 0.05 | 0.05 | 0.05 | 0.1 |
| | purified water | | residual | residual | residual | residual |
| Evaluation test results | less stickiness | | Δ | ⊚ | ○ | Δ |
| | emollient | | ○ | ○ | ○ | Δ |
| | hair repair and protection properties | | ⊚ | Δ | Δ | Δ |
| | low production costs | | ○ | X | X | ○ |
| | unpleasant creaky feeling upon rinsing | | ⊚ | ⊚ | Δ | Δ |

TABLE 8

| | | | Sample | | | | | | | Comparative Sample | |
|---|---|---|---|---|---|---|---|---|---|---|---|
| | | | 9 | 10 | 11 | 12 | 13 | 14 | 15 | 5 | 6 |
| Ingredient (wt %) | base material | (No.) | 9 | 9 | 9 | 9 | 9 | 9 | 9 | 10 | 11 |
| | | (cotent) | 1 | 1 | 1 | 1 | 1 | 5 | 5 | 1 | 1 |
| | base material | (No.) | 6 | 6 | 5 | 7 | 7 | 4 | 4 | 6 | 6 |
| | | (cotent) | 10 | 10 | 3 | 14 | 14 | 10 | 10 | 10 | 10 |
| | liquid lanolin | | — | — | — | — | — | — | — | — | — |
| | 90% lactic acid | | — | — | — | — | — | 0.66 | 0.66 | — | — |
| | myristyl alcohol | | 0.5 | 0.5 | 0.5 | — | — | — | — | 0.5 | 0.5 |
| | cetanol | | — | — | 2.5 | — | — | — | — | — | — |
| | highly polymerized polyethylene glycol | | — | 0.02 | — | — | 0.02 | — | 0.02 | — | — |
| | methylparaben | | 0.1 | 0.1 | 0.1 | 0.1 | 0.1 | 0.3 | 0.3 | 0.1 | 0.1 |
| | propylparaben | | 0.05 | 0.05 | 0.05 | 0.05 | 0.05 | 0.1 | 0.1 | 0.05 | 0.05 |
| | purified water | | residual | residual | residual | residual | residual | residual | residual | residual | residual |
| Evaluation test results | less stickiness | | ◎ | ◎ | ◎ | ◎ | ◎ | ◎ | ◎ | — | — |
| | emollient | | ◎ | ◎ | ◎ | ◎ | ◎ | ◎ | ◎ | ○ | ○ |
| | hair repair and protection properties | | ◎ | ◎ | ◎ | ◎ | ◎ | ◎ | ◎ | — | — |
| | low production costs | | ◎ | ◎ | ◎ | ◎ | ◎ | ◎ | ◎ | ○ | X |
| | unpleasant creaky feeling upon rinsing | | ◎ | ◎ | ◎ | Δ | ◎ | Δ | ◎ | ◎ | ◎ |
| | hair smoothness | | ◎ | ◎ | ◎ | ◎ | ◎ | ◎ | ◎ | Δ | Δ |
| | hair luster | | ◎ | ◎ | ◎ | ◎ | ◎ | ◎ | ◎ | Δ | ○ |

| | | | Comparative Sample | | Control | | |
|---|---|---|---|---|---|---|---|
| | | | 7 | 8 | 1 | 2 | 3 |
| Ingredient (wt %) | base material | (No.) | 11 | 10 | — | — | — |
| | | (cotent) | 1 | 5 | — | — | — |
| | base material | (No.) | 7 | 4 | 6 | 7 | 4 |
| | | (cotent) | 14 | 10 | 10 | 14 | 10 |
| | liquid lanolin | | — | — | 1 | 1 | 5 |
| | 90% lactic acid | | — | 0.66 | — | — | 0.66 |
| | myristyl alcohol | | — | — | 0.5 | — | — |
| | cetanol | | — | — | — | — | — |
| | highly polymerized polyethylene glycol | | — | — | — | — | — |
| | methylparaben | | 0.1 | 0.3 | 0.1 | 0.1 | 0.3 |
| | propylparaben | | 0.05 | 0.1 | 0.05 | 0.05 | 0.1 |
| | purified water | | residual | residual | residual | residual | residual |
| Evaluation test results | less stickiness | | — | — | — | — | — |
| | emollient | | ○ | ○ | — | — | — |
| | hair repair and protection properties | | — | — | — | — | — |
| | low production costs | | X | ○ | — | — | — |
| | unpleasant creaky feeling upon rinsing | | Δ | Δ | — | — | — |
| | hair smoothness | | ○ | Δ | — | — | — |
| | hair luster | | ○ | Δ | — | — | — |

TABLE 9

| | | | Sample | | | | | | Comparative Sample | |
|---|---|---|---|---|---|---|---|---|---|---|
| | | | 16 | 17 | 18 | 19 | 20 | 21 | 9 | 10 |
| Ingredient (wt %) | base material | (No.) | 12 | 12 | 12 | 12 | 12 | 12 | 13 | 13 |
| | | (cotent) | 2 | 2 | 2 | 2 | 5 | 5 | 2 | 2 |
| | base material | (No.) | 8 | 8 | 7 | 7 | 4 | 4 | 8 | 7 |
| | | (cotent) | 8 | 8 | 10 | 10 | 10 | 10 | 8 | 10 |
| | lanolin | | — | — | — | — | — | — | — | — |
| | 90% lactic acid | | — | — | — | — | 0.66 | 0.66 | — | — |
| | highly polymerized polyethylene glycol | | — | 0.02 | — | 0.02 | — | 0.02 | — | — |
| | methylparaben | | 0.1 | 0.1 | 0.1 | 0.1 | 0.3 | 0.3 | 0.1 | 0.1 |
| | propylparaben | | 0.05 | 0.05 | 0.05 | 0.05 | 0.1 | 0.1 | 0.05 | 0.05 |
| | purified water | | residual | residual | residual | residual | residual | residual | residual | residual |
| Evaluation test results | less stickiness | | ◎ | ◎ | ◎ | ◎ | ◎ | ◎ | — | — |
| | emollient | | ◎ | ◎ | ◎ | ◎ | ◎ | ◎ | ○ | ○ |
| | hair repair and protection properties | | ◎ | ◎ | ◎ | ◎ | ◎ | ◎ | ○ | ○ |
| | low production costs | | ◎ | ◎ | ◎ | ◎ | ◎ | ◎ | ○ | ○ |
| | unpleasant creaky feeling upon rinsing | | ◎ | ◎ | Δ | ◎ | Δ | ◎ | ◎ | Δ |
| | hair smoothness | | ◎ | ◎ | ◎ | ◎ | ◎ | ◎ | Δ | Δ |
| | hair rich taste | | ◎ | ◎ | ◎ | ◎ | ◎ | ◎ | ○ | ○ |

TABLE 9-continued

|  |  |  | Comparative Sample | | | Control | | |
|---|---|---|---|---|---|---|---|---|
|  |  |  | 11 | 12 | 13 | 4 | 5 | 6 |
| Ingredient (wt %) | base material | (No.) | 14 | 14 | 13 | — | — | — |
|  |  | (cotent) | 2 | 2 | 5 |  |  |  |
|  | base material | (No.) | 8 | 7 | 4 | 8 | 7 | 4 |
|  |  | (cotent) | 8 | 10 | 10 | 8 | 10 | 10 |
|  | lanolin |  | — | — | — | 2 | 2 | 2 |
|  | 90% lactic acid |  | — | — | 0.66 | — | — | 0.66 |
|  | highly polymerized polyethylene glycol |  | — | — | — | — | — | — |
|  | methylparaben |  | 0.1 | 0.1 | 0.3 | 0.1 | 0.1 | 0.3 |
|  | propylparaben |  | 0.05 | 0.05 | 0.1 | 0.05 | 0.05 | 0.1 |
|  | purified water |  | residual | residual | residual | residual | residual | residual |
| Evaluation test results | less stickiness |  | — | — | — | — | — | — |
|  | emollient |  | ○ | ○ | ○ | — | — | — |
|  | hair repair and protection properties |  | Δ | Δ | ◎ | — | — | — |
|  | low production costs |  | X | X | ○ | — | — | — |
|  | unpleasant creaky feeling upon rinsing |  | ◎ | Δ | Δ | — | — | — |
|  | hair smoothness |  | ○ | ○ | Δ | — | — | — |
|  | hair rich taste |  | ○ | ○ | ○ | — | — | — |

TABLE 10

|  |  |  | Sample | | | | | | Comparative Sample | |
|---|---|---|---|---|---|---|---|---|---|---|
|  |  |  | 22 | 23 | 24 | 25 | 26 | 27 | 14 | 15 |
| Ingredient (wt %) | base | (No.) | 15 | 15 | 15 | 15 | 15 | 15 | 16 | 17 |
|  |  | (cotent) | 1 | 1 | 1 | 1 | 3 | 3 | 1 | 1 |
|  | base | (No.) | 6 | 6 | 7 | 7 | 4 | 4 | 6 | 6 |
|  |  | (cotent) | 10 | 10 | 14 | 14 | 10 | 10 | 10 | 10 |
|  | hard lanolin |  | — | — | — | — | — | — | — | — |
|  | 90% lactic acid |  | — | — | — | — | 0.66 | 0.66 | — | — |
|  | cetanol |  | 0.5 | 0.5 | — | — | — | — | 0.5 | 0.5 |
|  | highly polymerized polyethylene glycol |  | — | 0.02 | — | 0.02 | — | 0.02 | — | — |
|  | methylparaben |  | 0.1 | 0.1 | 0.1 | 0.1 | 0.3 | 0.3 | 0.1 | 0.1 |
|  | propylparaben |  | 0.05 | 0.05 | 0.05 | 0.05 | 0.1 | 0.1 | 0.05 | 0.05 |
|  | purified water |  | residual | residual | residual | residual | residual | residual | residual | residual |
| Evaluation test results | less stickiness |  | ◎ | ◎ | ◎ | ◎ | ◎ | ◎ | — | — |
|  | emollient |  | ◎ | ◎ | ◎ | ◎ | ◎ | ◎ | — | — |
|  | hair repair and protection properties |  | ◎ | ◎ | ◎ | ◎ | ◎ | ◎ | — | — |
|  | low production costs |  | ◎ | ◎ | ◎ | ◎ | ◎ | ◎ | ○ | X |
|  | unpleasant creaky feeling upon rinsing |  | ◎ | ◎ | Δ | ◎ | Δ | ◎ | ◎ | ◎ |
|  | hair smoothness |  | ◎ | ◎ | ◎ | ◎ | ◎ | ◎ | Δ | ○ |
|  | hair coating properties |  | ◎ | ◎ | ◎ | ◎ | ◎ | ◎ | ○ | Δ |
|  | hair tension and stiffness |  | ◎ | ◎ | ◎ | ◎ | ◎ | ◎ | ○ | Δ |

|  |  |  | Comparative Sample | | Control | | |
|---|---|---|---|---|---|---|---|
|  |  |  | 16 | 17 | 7 | 8 | 9 |
| Ingredient (wt %) | base | (No.) | 17 | 16 | — | — | — |
|  |  | (cotent) | 1 | 3 |  |  |  |
|  | base | (No.) | 7 | 4 | 6 | 7 | 4 |
|  |  | (cotent) | 14 | 10 | 10 | 14 | 10 |
|  | hard lanolin |  | — | — | 1 | 1 | 3 |
|  | 90% lactic acid |  | — | 0.66 | — | — | 0.66 |
|  | cetanol |  | — | — | 0.5 | — | — |
|  | highly polymerized polyethylene glycol |  | — | — | — | — | — |
|  | methylparaben |  | 0.1 | 0.3 | 0.1 | 0.1 | 0.3 |
|  | propylparaben |  | 0.05 | 0.1 | 0.05 | 0.05 | 0.1 |
|  | purified water |  | residual | residual | residual | residual | residual |
| Evaluation test results | less stickiness |  | — | — | — | — | — |
|  | emollient |  | — | — | — | — | — |
|  | hair repair and protection properties |  | — | — | — | — | — |
|  | low production costs |  | X | ○ | — | — | — |
|  | unpleasant creaky feeling upon rinsing |  | Δ | Δ | — | — | — |
|  | hair smoothness |  | ○ | Δ | — | — | — |
|  | hair coating properties |  | Δ | ○ | — | — | — |
|  | hair tension and stiffness |  | Δ | ○ | — | — | — |

As is apparent from the results in Tables 7 to 10, Samples 1 to 27 containing the ingredient (I) provided less stickiness, superior emollient and hair repair and protection properties, and their production costs were very low.

As is apparent from the results in Table 7, Comparative Samples 1 and 4 containing vegetable sterol wax instead of the ingredient (I) provided stickiness. Comparative Samples 2 and 3 containing phytosteryl oleate instead of the ingredient (I) provided poor repair and protection properties, and their production costs were very high.

As is apparent from the results in Tables 7 to 10, Samples 2, 6, 8, 10, 13, 15, 17, 19, 21, 23, 25 and 27 containing highly polymerized polyethylene glycol could decrease or prevent unpleasant creaky feeling upon rinsing.

As is apparent from the results in Table 7, Sample 4 containing vaseline could decrease or prevent unpleasant creaky feeling upon rinsing.

As is apparent from the results in Table 8, Samples 9 to 15 containing the ingredient (I), the vegetable oil (II), the ingredients (III) and (IV) provided hair smoothness and luster having the same level or more of those of Controls 1 to 3 containing liquid lanolin instead of the ingredient (I), the vegetable oil (II), the ingredients (III) and (IV). In other words, the base consisting of the ingredient (I), the vegetable oil (II), the ingredients (III) and (IV) can be a substituent for the liquid lanolin. It can be concluded that the hair conditioner containing the ingredient (I), the vegetable oil (II), the ingredients (III) and (IV) can provide hair with a liquid lanolin-like feeling.

As is apparent from the results in Table 8, Comparative Samples 5 and 8 containing vegetable sterol wax or phytosteryl oleate instead of the ingredient (I), the vegetable oil (II), the ingredients (III) and (IV) provided poor liquid lanolin-like hair smoothness and luster.

As is apparent from the results in Table 9, Samples 16 to 21 containing the ingredient (I) and the hydrogenated vegetable oil (II) provided hair smoothness and luster having the same level or more of those of Controls 4 to 6 containing lanolin instead of the ingredient (I) and the hydrogenated vegetable oil (II). In other words, the base consisting of the ingredient (I) and the hydrogenated vegetable oil (II) can be a substitute for lanolin. It can be concluded that the hair conditioner containing the ingredient (I) and the hydrogenated vegetable oil (II) can provide hair with a lanolin-like feeling.

As is apparent from the results in Table 9, Comparative Samples 9 to 13 containing a vegetable sterol wax or phytosteryl oleate instead of the ingredient (I) and the hydrogenated vegetable oil (II) provided poor lanolin-like smoothness and rich taste.

As is apparent from the results in Table 10, Samples 22 to 27 containing the ingredient (I), the vegetable oil (II) and the hydrogenated vegetable oil (II) provided hair smoothness, film-formed feeling, and tension and stiffness having the same level or more of those of Controls 7 to 9 containing hard lanolin instead of the ingredient (I), the vegetable oil (II), and the hydrogenated vegetable oil (II). In other words, the base consisting of the ingredient (I), the vegetable oil (II) and the hydrogenated vegetable oil (II) can be a substitute for the hard lanolin. It can be concluded that the hair conditioner containing the ingredient (I), the vegetable oil (II) and the hydrogenated vegetable oil (II) can provide hair with a hard lanolin-like feeling.

As is apparent from the results in Table 10, Comparative Samples 14 to 17 containing a vegetable sterol wax or phytosteryl oleate instead of the ingredient (I), the vegetable oil (II) and the hydrogenated vegetable oil (II) provided poor hard lanolin-like hair smoothness, film-formed feeling, and tension and stiffness.

What is claimed is:

1. A method of preparing a hair cosmetic composition containing an additive which improves the feel thereof, consisting of the steps of:
    performing steam distillation of a vegetable oil to obtain a deodorized vegetable oil distillate;
    methyl-esterifying or ethyl-esterifying free fatty acids contained in the deodorized vegetable oil distillate to obtain an esterified deodorized vegetable oil distillate;
    contacting the esterified deodorized vegetable oil distillate with a basic anion-exchange resin to remove tocopherol therefrom and form a resultant distillate;
    distilling off volatile ingredients from the resultant distillate at a pressure of 1-0.005 Torr and a temperature of 150-160° C. to form a distillate product;
    esterifying phytosterols contained in the distillate product with at least one fatty acid having from sixteen to twenty carbon atoms to form an esterification reaction product;
    decoloring the esterification reaction product to form a decolored esterification reaction product;
    deodorizing the decolored esterification reaction product to form a cosmetic additive; and
    combining the cosmetic additive with at least one other cosmetic ingredient to form the cosmetic composition.

2. The method of claim 1, wherein the vegetable oil is at least one member selected from the group consisting of soybean oil, rape seed oil, cotton seed oil, corn oil and sunflower oil.

3. The method of claim 1, wherein the at least one fatty acid is at least one member selected from the group consisting of oleic acid, linoleic acid and stearic acid.

4. The method of claim 1, wherein the decolored esterification reaction product is deodorized by blowing water at a temperature of from 150-160° C. therethrough and under a pressure of from 10-0.1 Torr.

5. The method of claim 1, wherein the esterification reaction product is decolored by at least one member selected from the group consisting of active clay, acid clay, silica gel and an adsorbing resin.

6. The method of claim 1, wherein the at least one other cosmetic ingredient is at least one of a vegetable oil and a hydrogenated vegetable oil.

7. The method of claim 6, wherein the at least one other cosmetic ingredient comprises a sucrose fatty acid ester and a fatty acid having from 16-22 carbon atoms.

* * * * *